US008314269B2

(12) United States Patent  
Mansfield et al.

(10) Patent No.: US 8,314,269 B2
(45) Date of Patent: *Nov. 20, 2012

(54) N-(1-METHYL-2PHENYLETHYL)BENZAMIDE DERIVATIVES

(75) Inventors: Darren Mansfield, Bergisch Gladbach (DE); Pierre-Yves Coqueron, Lyons (FR); Heiko Rieck, Burscheid (DE); Philippe Desbordes, Lyons (FR); Alain Villier, Collonges au Mont d'Or (FR); Marie-Claire Grosjean-Cournoyer, Curis au Mont d'Or (FR); Pierre Genix, Lyons (FR)

(73) Assignee: Bayer Cropscience AG (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/094,664

(22) Filed: Apr. 26, 2011

(65) Prior Publication Data

US 2011/0237678 A1     Sep. 29, 2011

Related U.S. Application Data

(63) Continuation of application No. 12/085,300, filed as application No. PCT/EP2006/068717 on Nov. 21, 2006, now Pat. No. 7,951,973.

(30) Foreign Application Priority Data

Nov. 22, 2005 (EP) .................................. 05356201

(51) Int. Cl.
C07C 233/65 (2006.01)
A01N 37/18 (2006.01)
(52) U.S. Cl. ................... 564/185; 564/184; 514/617
(58) Field of Classification Search .................. 564/184, 564/185; 514/617
See application file for complete search history.

(56) References Cited

U.S. PATENT DOCUMENTS

| 4,221,815 | A | 9/1980 | Weyer et al. | |
| 7,259,183 | B2 * | 8/2007 | Conte-Mayweg et al. | ... 514/419 |
| 7,951,973 | B2 * | 5/2011 | Mansfield et al. | ............. 564/184 |

FOREIGN PATENT DOCUMENTS

| EP | 1389614 | 2/2004 |
| WO | WO 97/08135 | 3/1997 |

OTHER PUBLICATIONS

Borgna, P. et al.: IL Farmaco, Ed. Sc., vol. 33, No. 7, 1978, pp. 510-515, XP-09066592.
Database Beilstein, Institut zur Foerderung der Chemischen Wissenschaften; Beilstein Registry No. 9572000, )CP00238107-8, abstract & Fernandez-Ferri, Patricia et al.: Eur. J.Med. Chem. Chim, Tier., vol. 38, No. 3, 2003, pp. 289-296.
Database Beilstein, Institut zur Foerderung der Chemischen Wissenschaften; Beilstein Registry No. 2699915, XP0023810, abstract & Bhattacharya: Indian Journal Chemistry, vol. 6, 1968, pp. 341-343.
Database Beilstein, Institut zur Foerderung der Chemischen Wissenschaften; Beilstein Registry No. 2143583, XP002381080, abstract, & Borgna et al.: Farmaco Ed. Sci., vol. 33, 1978, pp. 510-513.
Database Beilstein, Institut zur Foerderung der Chemischen Wissenschaften; Beilstein Registry No. 8494699, XP002381081, abstract & Jullian, Valerie et al.: Journal Organic Chemistry, vol. 7, 2000, pp. 1319-1326.
Database Beilstein, Institut zur Foerderung der Chemischen Wissenschaften; Beilstein Registry No. 6728087, XP002381082, abstract & Okazaki, Renji et al.: J. Chem. Soc. Chem. Commun., vol. 3, 1984, pp. 192-193.
Database Beilstein, Institut zur Foerderung der Chemischen Wissenschaften; Beilstein Registry No. 6345320, XP002381083, abstract, & WIPF, Peter et al.: Journal Organic Chemistry, vol. 58, No. 12, 1993, pp. 3455-3459.
Database Beilstein, Institut zur Foerderung der Chemischen Wissenschaften; Beilstein Registry No. 4258720, XP002381084, abstract, & Kita, Yasuyuki et al: Journal Organic Chemistry, vol. 56, No. 1, 1991, pp. 435-438.
Database Beilstein, Institut zur Foerdening der Chemischen Wissenschaften; Beilstein Registry No. 3071952, XP002381085, abstract, & Matin, S.B. et al: J. Pharm. Sci., vol. 61, 1972, pp. 1235-1240.
Database Beilstein, Institut zur Foerderung der Chemischen Wissenschaften; Beilstein Registry No. 8496320, XP002381086 abstract & Hoffman, Brian et al.: J. Med. Chem., vol. 42, No. 17, 1999, pp. 3217-3226.
Database Beilstein, Institut zur Foerderung der Chemischen Wissenschaften; Beilstein Registry No. 7545284, XP002381087, abstract & Kaufman, M.S.: J. Mass. Spectrom., vol. 31, No. 6, 1996, pp. 913-920.
Database Beilstein, Institut zur Foerderung der Chemischen Wissenschaften; Beilstein Registry No. 5820099, XP002381088, abstract & Lamas, Carlos et al.: Tetrahedron Letters, vol. 33, No. 38, 1992, pp. 5653-5654.
Database Beilstein, Institut zur Foerderung der Chemischen Wissenschaften; Beilstein Registry No. 5087725, XP002381089, abstract & Barker, John M. et al: J. Chem. Soc. Perkin Trans., vol. 1, 1985, pp. 275-282.

(Continued)

Primary Examiner — Shailendra Kumar
(74) Attorney, Agent, or Firm — Ostrolenk Faber LLP

(57) ABSTRACT

A compound of general formula (I) is disclosed.

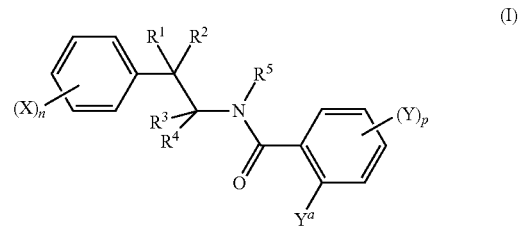

A process for preparing this compound, a fungicidal composition comprising a compound of general formula (I), and method for treating plants by applying a compound of general formula (I) or a composition comprising it are disclosed.

13 Claims, No Drawings

OTHER PUBLICATIONS

Database Beilstein, Institut zur Foerderung der Chemischen Wissenschaften; Beilstein Registry No. 3595966, XP002381090, abstract & Coquerel, Gerard et al.: Tetrahedron Letters, vol. 31, No. 15, 1990, pp. 2143-2144.

Database Beilstein, Institut zur Foerderung der Chemischen Wissenschaften; Beilstein Registry No. 3074174, XP002381091, abstract & Matin, S.B. et al.: J. Pharm. Sci., vol. 61, 1972, pp. 1235-1240.

Database Beilstein, Institut zur Foerderung der Chemischen Wissenschaften; Beilstein Registry No. 2157436, XP002381092, abstract & Viel, C. et al.: Bull. Soc. Chm Fr., 1966, pp. 1956-1966.

Database Beilstein, Institut zur Foerderung der Chemischen Wissenschaften; Beilstein Registry No. 270217, XP002381093, abstract & Bhattacharya: Indian J. Chem., vol. 6, 1968, pp. 341-343.

Database Beilstein, Institut zur Foerderung der Chemischen Wissenschaften; Beilstein Registry No. 8496470, XP002381094, abstract & Hoffman, B. et al: J. Med. Chem., vol. 42, No. 17, 1999, pp. 3217-3226.

Database Beilstein, Institut zur Foerderung der Chemischen Wissenschaften; Beilstein Registry No. 7138838, XP002381095, abstract & Cortes, Eduardo C. et al.: J. Heterocycl. Chem., vol. 31, No. 6, 1994, pp. 1425-1428.

Database Beilstein, Institut zur Foerderung der Chemischen Wissenschaften; Beilstein Registry No. 6216660, XP002381096, abstract & Meise, W. et al.. Arch. Pharm., vol. 322, 1989, pp. 245-252.

Database Beilstein, Institut zur Foerderung der Chemischen Wissenschaften; Beilstein Registry No. 8497220, XP002381097, abstract & Hoffman, Brian et al.: J. Med. Chem., vol. 42, No. 17, 1999, pp. 3217-3226.

Marvin S. Kaufman, et al.,"Negative-ion Chemical Ionization of Amphetamine Derivatives," Journal of Mass Spectrometry, vol. 31, pp. 913-920 (1996).

Bhabatosh Bhattacharya, "Isoquinoline Derivatives: Part XVIII—Formation of I-Alkyl-(or alkaryl or aryl)-3-methyl-7-chloro-(or 5-chloro)-isoquinolines," Indian Journal of Chemistry, vol. 6 (7), 341-5, (Jul. 1968).

* cited by examiner

N-(1-METHYL-2PHENYLETHYL)BENZAMIDE DERIVATIVES

This application is a continuation application of U.S. application Ser. No. 12/085,300 filed on Sep. 15, 2008, now U.S. Pat. No. 7,951,973, which claims priority to International Application No. PCT/EP2006/068717 filed on Nov. 21, 2006, which claims priority to European Application No. 05356201.3 filed on Nov. 22, 2005.

The present invention relates to novel N-(1methyl-2-phenylethyl)benzamide derivatives, their process of preparation, their use as fungicides, particularly in the form of fungicidal compositions, and methods for the control of phytopathogenic fungi of plants using these compounds or their compositions.

International patent application WO 97/08135 discloses preparation of acylaminosalicylamides derivatives and their use as fungicide. However, compounds according to the present invention are not covered neither disclosed in that patent application.

It is always of high-interest in the field of agrochemicals to use novel pesticidal compounds with a high efficacy to limit and reduce the risk of appearance of resistant strains in the fungi to be treated.

We have now found a new family of compounds which shows a fungicidal activity.

Accordingly, the present invention relates to a N-(1methyl-2phenylethypbenzamide derivative of general formula (I)

(I)

in which:
n is 1, 2, 3, 4 or 5;
p is 1, 2, 3 or 4;
X is the same or different and is a halogen atom, a nitro group, a cyano group, an amino group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N-$C_1$-$C_8$-alkyloxycarbamoyl, a $C_1$-$C_8$-alkoxycarbamoyl, a N-$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_2$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkyl-sulphonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl or a phenylamino;
$R^1$ and $R^3$ are the same or different and are a hydrogen atom, a halogen atom, a $C_1$-$C_6$-alkyl or a $C_1$-$C_6$-alkyl-$C_3$-$C_7$-cycloalkyl;
$R^3$ and $R^4$ are the same or different and are a hydrogen atom, a $C_1$-$C_8$-alkyl or a $C_1$-$C_6$-alkyl-$C_3$-$C_7$-cycloalkyl;
$R^5$ is a hydrogen atom, a $C_1$-$C_6$-alkyl or a $C_3$-$C_7$-cycloalkyl;
Y is the same or different and is a hydrogen atom, a halogen atom, a $C_1$-$C_6$-alkyl or a $C_1$-$C_6$-halogenoalkyl; and
$Y^a$ is a halogen atom, a $C_1$-$C_8$-alkyl or a $C_1$-$C_8$-halogenoalkyl;
as well as its salts, N-oxides, metallic complexes, metalloidic complexes and optically active isomers;
with the proviso that compound of general formula (I) is different from:
2,3,4,5,6-pentafluoro-N-[2-(2,5-dimethoxyphenyl)-1-methylethyl]-benzamide;
2,3,4,5,6-pentafluoro-N-[2-(4-methoxyphenyl)-1-methylethyl]-benzamide;
2,3,4,5,6-pentafluoro-N-[1-methyl-2-(3,4,5-trimethoxyphenyl)ethyl]-benzamide;
2,3,4,5,6-pentafluoro-N-[1-(phenylmethyl)ethyl-2,2,2-d3]-benzamide;
2,3,4,5,6-pentafluoro-N-[2-(4-methoxyphenyl)-1-methylethyl]-N-methyl-benzamide;
2,3,4,5,6-pentafluoro-N-[2-(2-methoxyphenyl)-1-methylethyl]-N-methyl-benzamide;
2,3,4,5,6-pentafluoro-N-[2-(4-chlorophenyl)-1-methylethyl]-benzamide;
2-chloro-N-[2-(3-chloro-4-methoxyhenyl)ethyl]-benzamide;
N-[2-(2-bromophenyl)ethyl]-2-iodobenzamide;
2-bromo-N-[2-(3,4-dimethoxyphenyl)ethyl]-benzamide;
2,4-dichloro-N-[1-methyl-2-(3-trifluoromethylphenyl) ethyl]-benzamide;
2-chloro-N-[2-(3,4-dimethoxyphenyl)ethyl]-benzamide;
2-chloro-N-[2-(4-chlorophenyl)-1-methyl-ethyl]-benzamide;
N-[2-(3-chloro-4-methoxyphenyl)ethyl]-2-methylbenzamide;
N-[2-(3,4-dimethoxyphenyl)ethyl]-2-methylbenzamide;
2-(2-chloroethyl)-N-[2-(4-methoxyphenyl)ethyl]-benzamide; and
N-[2-(3-chloro-4-methoxyphenyl)ethyl]-2,6-dimethylbenzamide.

In the context of the present invention:
halogen means fluorine, bromine, chlorine or iodine.
carboxy means —C(=O)OH;
carbonyl means —C(=O)—;
carbamoyl means —C(=O)NH$_2$;
N-hydroxycarbamoyl means —C(=O)NHOH;
an alkyl group, an alkenyl group, and an alkynyl group as well as moieties containing these terms, can be linear or branched; and
heteroatom means sulphur, nitrogen or oxygen.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of general formula (I) wherein X represents a hydroxy, a sulfanyl group or an amino group may be found in its tautomeric form resulting from the shift of the proton of said hydroxy, sulfanyl or amino group. Such tautomeric forms of such compounds are also part of the present invention. More generally speaking, all tautomeric forms of compounds of general formula (I) wherein X represents a hydroxy, a sulfanyl group or an amino group, as well as the tautomeric forms of the compounds which can optionally be used as intermediates in the preparation processes, and which will be defined in the description of these processes, are also part of the present invention.

According to the present invention, the phenyl group may be substituted in any position by $(X)_n$, in which X and n are as defined above. Preferably, the present invention relates to N-(1methyl-2-phenylethyl)benzamide derivative of general formula (I) in which the different characteristics may be chosen alone or in combination as being:

as regards n, n is 1, 2 or 3. More preferably n is 1 or 2; and
as regards X, X is chosen as being as being a halogen atom, a (hydroxyimino)-$C_1$-$C_6$-alkyl group, a $C_1$-$C_8$-alkyl, a $C_1$-$C_8$-halogenoalkyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl or a ($C_1$-$C_6$-allynyloxyimino)-$C_1$-$C_6$-alkyl. More preferably X is chosen as being a halogen atom or a $C_1$-$C_8$-halogenoalkyl having 1 to 5 halogen atoms.

According to the present invention, the carbon atoms of the carboxamide moiety of the compound of formula (I) are substituted by $R^1$, $R^2$, $R^3$ and $R^4$; $R^1$, $R^2$, $R^3$ and $R^4$ being as defined above. Preferably, the present invention also relates to N-(1-methyl-2-phenylethyl)benzamide derivatives of general formula (I) in which the different characteristics may be chosen alone or in combination as being:

as regards $R^1$ and $R^2$, $R^1$ and $R^2$ are chosen, independently of each other, as being a hydrogen atom or a halogen atom;
as regards $R^3$ and $R^4$, $R^3$ and $R^4$ are chosen, independently of each other, as being a hydrogen atom or $C_1$-$C_6$-alkyl. More preferably $R^3$ is chosen as being a methyl group and $R^4$ is chosen as being a hydrogen atom.

According to the present invention, the nitrogen atom of the carboxamide moiety of the compound of formula (I) is substituted by $R^5$, $R^5$ being a hydrogen atom, a $C_1$-$C_6$-alkyl or a $C_3$-$C_7$-cycloalkyl. Preferably, the $C_3$-$C_7$-cycloalkyl is cyclopropyl.

According to the present invention, the ortho-substituted phenyl group may be substituted in ortho position by $Y^a$ and in any other position by $(Y)_p$, in which $Y^a$, Y and p are as defined above. Preferably, the present invention relates to N-(1-methyl-2-phenylethyl)benzamide derivative of general formula (I) in which the different characteristics may be chosen alone or in combination as being:

as regards $Y^a$, $Y^a$ is chosen as being a halogen atom, a $C_1$-$C_6$-alkyl or a $C_1$-$C_6$-halogenoalkyl having 1 to 5 halogen atoms;
as regards p, p is 1 or 2. More preferably p is 1; and
as regards Y, Y is chosen as being a hydrogen atom or a halogen atom.

The present invention also relates to a process for the preparation of the compound of general formula (I). Thus, according to a further aspect of the present invention there is provided a process for the preparation of compound of general formula (I) as defined above, which comprises reacting a 1-alkyl-2-phenylethylamine derivative of general formula (II) or one of its salt

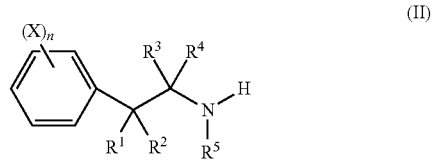

(II)

in which $R^1$, $R^2$, $R^3$, $R^4$, $R^5$, X and n, are as defined above; with a carboxylic acid derivative of the general formula (III)

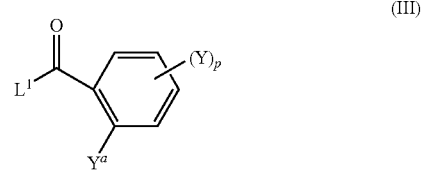

(III)

in which:
$Y^a$, Y and p are as defined above; and
$L^1$ is a leaving group chosen as being a halogen atom, a hydroxyl group, —$OR^6$, —$OCOR^6$, $R^6$ being a $C_1$-$C_6$ alkyl, a $C_1$-$C_6$ haloalkyl, a benzyl, 4-methoxybenzyl, pentafluorophenyl or a group of formula

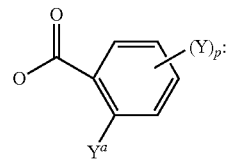

in the presence of a catalyst and, if $L^1$ is a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case $L^1$ is a hydroxyl group, the process according to the present invention is conducted in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

When $R^5$ is a hydrogen atom, the above mentioned process for the preparation of compound of general formula (I) may optionally be completed by a further step according to the following reaction scheme:

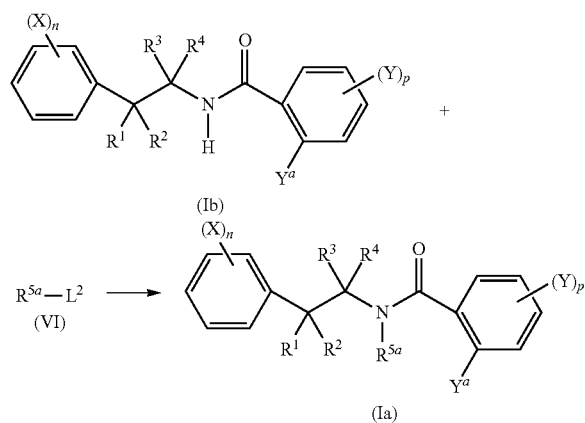

in which:

$R^1$, $R^2$, $R^3$, $R^4$, X, n, $Y^a$, Y and p are as defined above;

$L^2$ is a leaving group chosen as being a halogen atom, a 4-methyl phenylsulfonyloxy or a methylsulfonyloxy; and $R^{5a}$ is a $C_1$-$C_6$-alkyl group or a $C_3$-$C_7$-cycloalkyl; comprising the reaction of a compound of general formula (Ib) with a compound of general formula (VI) to provide a compound of general formula (Ia).

Depending on the definition of $R^1$, $R^2$, $R^3$, $R^4$, $R^5$, X, and n, amine derivatives of general formula (II) may be prepared by different processes. One example (A) of such a process may be when:

$R^1$, $R^2$, $R^3$, $R^5$, X and n are as defined above; and $R^4$ is a hydrogen atom;

then, the amine derivative of general formula (II) may be prepared according to a process which comprises:

a first step according to reaction scheme A-1:

Scheme A-1

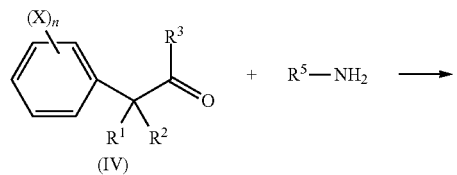

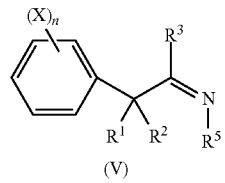

in which $R^1$, $R^2$, $R^3$, $R^5$, X and n are as defined above; comprising the reaction of a compound of general formula (IV) with an amine of formula $R^5$—$NH_2$ to provide an imine derivative of general formula (V);

a second step according to scheme A-2:

Scheme A-2

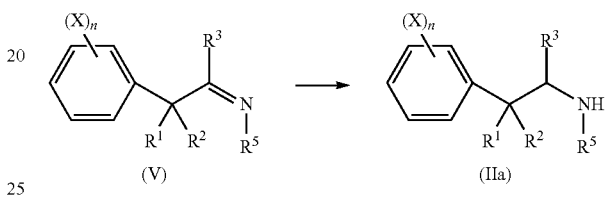

in which $R^1$, $R^2$, $R^3$, $R^5$, X and n are as defined above; comprising the reduction of an imine derivative of general formula (V) by hydrogenation or by an hydride donor, in the same or a different pot to provide an amine derivative of general formula (IIa) or one of its salt. Preferably, the hydride donor is chosen as being metal or metalloid hydrides such as $LiAlH_4$, $NaBH_4$, $NaBH_3CN$, $KBH_4$, $B_2H_6$.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesise.

On the basis of his general knowledge and of available publications, the skilled worker will also be able to prepare intermediate compound of formula (V) according to the present invention.

The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous. Examples of suitable fungicide mixing partners may be selected in the following lists 1) a compound capable to inhibit the nucleic acid synthesis like benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid;

2) a compound capable to inhibit the mitosis and cell division like benomyl, carbendazim, diethofencarb, ethaboxam, fuberidazole, pencycuron, thiabendazole thiophanate-methyl, zoxamide;

3) a compound capable to inhibit the respiration for example
as CI-respiration inhibitor like diflumetorim;
as CII-respiration inhibitor like boscalid, carboxin, fenfuram, flutolanil, furametpyr, furmecyclox, mepronil, oxycarboxine, penthiopyrad, thifluzamide;
as CHI-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

4) a compound capable of to act as an uncoupler like dinocap, fluazinam, meptyldinocap;

5) a compound capable to inhibit ATP production like fentin acetate, fentin chloride, fentin hydroxide, silthiofam;

6) a compound capable to inhibit AA and protein biosynthesis like andoprim, blasticidin-S, cyprodinil, kasugamycin, kasugamycin hydrochloride hydrate, mepanipyrim, pyrimethanil;

7) a compound capable to inhibit the signal transduction like fenpiclonil, fludioxonil, quinoxyfen;

8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

10) a compound capable to inhibit cell wall synthesis like benthiavalicarb, bialaphos, dimethomorph, flumorph, iprovalicarb, mandipropamid, polyoxins, polyoxorim, validamycin A;

11) a compound capable to inhibit melanine biosynthesis like carpropamid, diclocymet, fenoxanil, phthalide, pyroquilon, tricyclazole;

12) a compound capable to induce a host defence like acibenzolar-S-methyl, probenazole, tiadinil;

13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, thiram, tolylfluanid, zineb, ziram;

14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidin-7-amine, 5-chloro-7-(4-methylpiperidin-1-yl)-6-(2,4,6-trifluorophenyl) [1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidin-7-amine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(4-{[3-(4-chlorophenyl)prop-2-yn-1-yl]oxy}-3-methoxyphenyl)ethyl]-N<-(methylsulfonyl)valinamide, N-{(Z)-[(cyclopropylmethoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-, 1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, tecloftalam, tecnazene, triazoxide, trichlamide, valiphenal, zarilamid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

Among the diseases of plants or crops that can be controlled by the method according to the present invention, mention may be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;

Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondita*;
*Uromyces* diseases, caused for example by *Uromyces appendiculatus*;

Oomycete diseases such as:
  Bremia diseases, caused for example by *Bremia lactucae;*
  Peronospora diseases, caused for example by *Peronospora pisi* or *P. brassicae;*
  Phytophthora diseases, caused for example by *Phytophthora infestans;*
  Plasmopara diseases, caused for example by *Plasmopara viticola;*
  Pseudoperonospora diseases, caused for example by *Pseudoperonospora humuli* or *Pseudoperonospora cubensis;*
  Pythium diseases, caused for example by *Pythium ultimum;*
Leafspot, leaf blotch and leaf blight diseases such as:
  Alternaria diseases, caused for example by *Alternaria solani;*
  Cercospora diseases, caused for example by *Cercospora beticola;*
  Cladiosporum diseases, caused for example by *Cladiosporium cucumerinum;*
  Cochliobolus diseases, caused for example by *Cochliobolus sativus;*
  Colletotrichum diseases, caused for example by *Colletotrichum lindemuthanium;*
  Cycloconium diseases, caused for example by *Cycloconium oleaginum;*
  Diaporthe diseases, caused for example by *Diaporthe citri;*
  Elsinoe diseases, caused for example by *Elsinoe fawcettii;*
  Gloeosporium diseases, caused for example by *Gloeosporium laeticolor;*
  Glomerella diseases, caused for example by *Glomerella cingulata;*
  Guignardia diseases, caused for example by *Guignardia bidwelli;*
  Leptosphaeria diseases, caused for example by *Leptosphaeria maculans; Leptosphaeria nodorum;*
  Magnaporthe diseases, caused for example by *Magnaporthe grisea;*
  Mycosphaerella diseases, caused for example by *Mycosphaerella graminicola; Mycosphaerella arachidicola; Mycosphaerella fijiensis;*
  Phaeosphaeria diseases, caused for example by *Phaeosphaeria nodorum;*
  Pyrenophora diseases, caused for example by *Pyrenophora teres;*
  Ramularia diseases, caused for example by *Ramularia collo-cygni;*
  Rhynchosporium diseases, caused for example by *Rhynchosporium secalis;*
  Septoria diseases, caused for example by *Septoria apii* or *Septoria lycopercisi;*
  Typhula diseases, caused for example by *Typhula incarnata;*
  Venturia diseases, caused for example by *Venturia inaequalis;*
Root and stem diseases such as:
  Corticium diseases, caused for example by *Corticium graminearum;*
  Fusarium diseases, caused for example by *Fusarium oxysporum;*
  Gaeumannomyces diseases, caused for example by *Gaeumannomyces graminis;*
  Rhizoctonia diseases, caused for example by *Rhizoctonia solani;*
  Tapesia diseases, caused for example by *Tapesia acuformis;*
  Thielaviopsis diseases, caused for example by *Thielaviopsis basicola;*
Ear and panicle diseases such as:
  Alternaria diseases, caused for example by *Alternaria* spp.;
  Aspergillus diseases, caused for example by *Aspergillus flavus;*
  Cladosporium diseases, caused for example by *Cladosporium* spp.;
  Claviceps diseases, caused for example by *Claviceps purpurea;*
  Fusarium diseases, caused for example by *Fusarium culmorum;*
  Gibberella diseases, caused for example by *Gibberella zeae;*
  Monographella diseases, caused for example by *Monographella nivalis;*
Smut and bunt diseases such as:
  Sphacelotheca diseases, caused for example by *Sphacelotheca reiliana;*
  Tilletia diseases, caused for example by *Tilletia caries;*
  Urocystis diseases, caused for example by *Urocystis occulta;*
  Ustilago diseases, caused for example by *Ustilago nuda;*
Fruit rot and mould diseases such as:
  Aspergillus diseases, caused for example by *Aspergillus flavus;*
  Botrytis diseases, caused for example by *Botrytis cinerea;*
  Penicillium diseases, caused for example by *Penicillium expansum;*
  Sclerotinia diseases, caused for example by *Sclerotinia sclerotiorum;*
  Verticilium diseases, caused for example by *Verticilium alboatrum;*
Seed and soilborne decay, mould, wilt, rot and damping-off diseases:
  Fusarium diseases, caused for example by *Fusarium culmorum;*
  Phytophthora diseases, caused for example by *Phytophthora cactorum;*
  Pythium diseases, caused for example by *Pythium ultimum;*
  Rhizoctonia diseases, caused for example by *Rhizoctonia solani;*
  Sclerotium diseases, caused for example by *Sclerotium rolfsii;*
  Microdochium diseases, caused for example by *Microdochium nivale;*
Canker, broom and dieback diseases such as:
  Nectria diseases, caused for example by *Nectria galligena;*
  Blight diseases such as:
  Monilinia diseases, caused for example by *Monilinia laxa;*
Leaf blister or leaf curl diseases such as:
  Taphrina diseases, caused for example by *Taphrina deformans;*
Decline diseases of wooden plants such as:
  Esca diseases, caused for example by *Phaemoniella clamydospora;*
Diseases of flowers and Seeds such as:
  Botrytis diseases, caused for example by *Botrytis cinerea;*
Diseases of tubers such as:
  Rhizoctonia diseases, caused for example by *Rhizoctonia solani.*

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

The aspects of the present invention will now be illustrated with reference to the following tables of compounds and examples. The following Table illustrates in a non-limiting manner examples of fungicidal compounds according to the present invention. In the following Examples, M+1 (or M−1) means the molecular ion peak, plus or minus 1 a.m.u. (atomic mass units) respectively, as observed in mass spectroscopy and M (ApcI+) means the molecular ion peak as it was found via positive atmospheric pressure chemical ionisation in mass spectroscopy.

| Compound | $R^1$ | $R^2$ | $R^3$ | $R^4$ | $R^5$ | $X^1$ | $X^2$ | $X^3$ | $X^4$ | $X^5$ | $Y^1$ | $Y^2$ | $Y^3$ | $Y^4$ | $Y^a$ | (M + 1) |
|---|---|---|---|---|---|---|---|---|---|---|---|---|---|---|---|---|
| 1 | H | H | Me | H | H | H | H | Cl | H | H | H | H | H | H | CF3 | 342 |
| 2 | H | H | Me | H | Cyclopropyl | H | H | Cl | H | H | H | H | H | H | CF3 | 382 |
| 3 | H | H | Me | H | Cyclopropyl | H | H | Cl | H | H | H | H | H | H | Br | 392 |
| 4 | H | H | Me | H | Cyclopropyl | H | H | Cl | H | H | H | H | H | H | I | 440 |
| 5 | H | H | Me | H | Cyclopropyl | H | H | Cl | H | H | H | H | H | H | Cl | 348 |
| 6 | H | H | Me | H | Cyclopropyl | H | H | Cl | H | H | H | H | H | H | Me | 328 |
| 7 | H | H | Me | H | Cyclopropyl | H | H | Cl | H | H | H | H | H | H | CHF2 | 363 |
| 8 | H | H | Me | H | H | H | H | Cl | H | H | H | H | H | Cl | Cl | 342 |
| 9 | H | H | Me | H | H | H | H | Cl | H | H | H | H | H | H | Br | 352 |
| 10 | H | H | Me | H | H | H | H | Cl | H | H | H | H | H | H | CHF2 | 324 |

EXAMPLES OF PROCESS FOR THE PREPARATION OF THE COMPOUND OF GENERAL FORMULA (I)

Preparation of 2,6-dichloro-N-[2-(4-chlorophenyl)-1-methylethyl]benzamide, (Compound 8)

100 mg of 1-(4-chlorophenyl)propan-2-amine hydrochloride (0.728 mmol) and 0.10 ml of triethylamine (0.728 mmol) are diluted in 3 ml of dichloromethane at room temperature, 152 mg of 2,6-dichlorobenzoyl chloride (0.728 mmol) are added to the reaction mixture. After 24 hours of stirring, 20 ml of DCM an 10 ml of saturated solution of ammonium chloride are added to the reaction mixture.

After separation, the organic phase is washed with 10 ml of a saturated solution of sodium bicarbonate.

After separation over magnesium sulphate, filtration and concentration in vacuo, 0.24 g of essentially pure 2,6-dichloro-N-[2-(4-chlorophenyl)-1-methylethyl]benzamide are obtained (yield=93%).

[M+1]=342

Preparation of N-[2-(4-chlorophenyl)-1-methylethyl]-N-cyclopropyl-2-(difluoromethyl)benzamide (Compound 7)

Preparation of N-[2-(4-chlorophenyl)-1-methylethyl] cyclopropanamine hydrochloride Under argon are mixed, in 150 ml of methanol, 10.1 g of cyclopropylamine (0.177 mol) and 12.6 ml of acetic acid (0.221 mol). 15.0 g of 1-(4-chlorophenyl)acetone (0.088 mol) and 15 g of 3 Å molecular sieves are then added. The reaction mixture is refluxed for 3 hours. After cooling to room temperature, 8.34 g of sodium cyanoborohydride (0.13 mol) are added to the reaction mixture which is refluxed again for 3 hours. After one night at room temperature, 3 g of cyanoborhydride (0.048 mol) and 8 ml of acetic acid (0.126 mol) are added to the reaction mixture which is refluxed for three hours. After cooling to room temperature, filtration over celite and concentration in vacuo, 250 ml of dichloromethane and 400 ml of NaOH 1M are added to the reaction mixture.

After separation, the aqueous phase is extracted with 250 ml of dichloromethane, the combined organic phases are washed with 1550 ml of water and 200 ml of brine.

After drying over magnesium sulphate, filtration and concentration, the crude amine is precipitated with HCl 2M in ether to yield to 19.06 g of N-[2-(4-chlorophenyl)-1-methylethyl]cyclopropanamine hydrochloride (yield=88%).

[M+1-HCl]=210.

Preparation of N-[2-(4-chlorophenyl)-1-methylethyl]-N-cyclopropyl-2-(difluoromethyl)benzamide 300 mg of N-[2-(4-chlorophenyl)-1-methylethyl]cyclopropanamine hydrochloride (1.218 mmol), 220 mg of 2-(difluoromethyl)benzoic acid (1.28 mmol), 16 mg of 1-hydroxybenzotriazole (0.12 mmol), 256 mg of 1-(3-dimethylaminopropyl)-3-ethylcarbodiimide hydrochloride (1.34 mmol) and 0.171 ml of TEA (1.22 mmol) are refluxed in 10 ml of dichloromethane for one hour. After 48 hours at room temperature, the reaction is quenched with 5 ml of HCl 0.5M.

After separation, the organic phase is washed with 5 ml of water and 5 ml of a saturated solution of sodium bicarbonate, dried over magnesium sulphate, filtered and concentrated in vacuo. The crude product is flash-chromatographed on silica with heptane/EtOAc to yield to 149 mg of N-[2-(4-chlorophenyl)-1-methylethyl]-N-cyclopropyl-2-(difluoromethyl)benzamide (yield=37%).

[M+1]=363.

Examples of Biological Activity of the Compound of General Formula (I)

Example A

In Vivo Test on *Alternaria brassicae* (Leaf Spot of Crucifers)

The active ingredients tested are prepared by homogenisation in a mixture of acetone/tween/DMSO, then diluted with water to obtain the desired active material concentration.

Radish plants (Pernot variety), sown on a 50/50 peat soil-pozzolana substrate in starter cups and grown at 18-20° C., are treated at the cotyledon stage by spraying with the active ingredient prepared as described above.

Plants, used as controls, are treated with the mixture of acetone/tween/DMSO/water not containing the active material.

After 24 hours, the plants are contaminated by spraying them with an aqueous suspension of *Alternaria brassicae* spores (40,000 spores per cm$^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants.

Under these conditions, good (at least 70%) or total protection is observed at a dose of 500 ppm with the following compounds: 1, 9 and 10.

Example B

In Vivo Test on *Pyrenophora teres* (Barley Net Blotch)

The active ingredients tested are prepared by homogenisation in a mixture of acetone/tween/DMSO, then diluted with water to obtain the desired active material concentration.

Barley plants (Express variety), sown on a 50/50 peat soil-pozzolana substrate in starter cups and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) or total protection is observed at a dose of 500 ppm with the following compound: 1.

Example C

In Vivo Test on *Mycosphaerella graminicola* (Wheat Leaf Spot)

The active ingredients tested are prepared by homogenisation in a mixture of acetone/tween/DMSO, then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 1, 9 and 10.

The invention claimed is:

1. A compound derivative of formula (I)

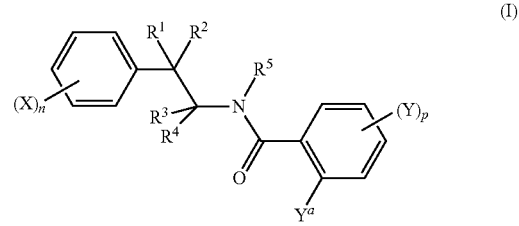

is which:

n is 1, 2, 3, 4 or 5;

p is 1, 2, 3 or 4;

each X is independently selected from the group consisting of a halogen atom, a nitro group, a cyano group, an amino group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_1$-$C_8$-halogenocycloalkyl having 1 to 5 halogen atoms, a $C_1$-$C_8$-alkylcarbonyl, a $C_3$-$C_8$-halogenoalkylcarbonyl having 1 to 5 halogen atoms, a $C_1$-$C_8$-alkylcarbamoyl, a di-$C_1$-$C_8$-alkylcarbamoyl, a N-$C_1$-$C_8$-alkyloxycarbamoyl, a $C_1$-$C_8$-alkoxycarbamoyl, a N-$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkysulfinyl having 1 to 5 halogen atoms, a $C_1$-$C_8$-alkylsulonyl, a $C_1$-$C_8$-halogenoalkylsulfonyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a (benzyloxyimino)-$C_1$-$C_6$-alkyl, a benzyloxy, a benzylsulfanyl, a benzylamino, a phenoxy, a phenylsulfanyl and a phenylamino;

$R^1$ and $R^2$ are independently selected from the group consisting of a hydrogen atom, a halogen atom, a $C_1$-$C_6$-alkyl and a $C_1$-$C_6$-alkyl-$C_3$-$C_7$-cycloalkyl;

$R^3$ and $R^4$ are independently selected from the group consisting of a hydrogen atom, a $C_1$-$C_8$-alkyl and a $C_1$-$C_6$-alkyl-$C_3$-$C_7$-cycloalkyl;

$R^5$ is selected from the group consisting of a hydrogen atom, a $C_1$-$C_6$-alkyl and a $C_3$-$C_7$-cycloalkyl;

each Y is independently selected from the group consisting of a hydrogen atom, a halogen atom, a $C_1$-$C_6$-alkyl and a $C_1$-$C_6$-halogenoalkyl; and $Y^a$ is selected from the group consisting of a halogen atom, a $C_1$-$C_8$-alkyl and a $C_1$-$C_8$-halogenoalkyl;

as well as its salts, N-oxides, metallic complexes, metalloidic complexes and optically active isomers;

with the proviso that compound of general formula (I) is different from:

2,3,4,5,6-pentafluoro-N-[2-(2,5-dimethoxyphenyl)-1-methylethyl]-benzamide;

2,3,4,5,6-pentafluoro-N-[2-(4-methoxyphenyl)-1-methylethyl]-benzamide;

2,3,4,5,6-pentafluoro-N-[1-methyl-2-(3,4,5-trimethoxyphenyl)ethyl]-benzamide;

2,3,4,5,6-pentafluoro-N-[1-(phenylmethyl)ethyl-2,2,2-d3]-benzamide;

2,-3,4,5,6-pentafluoro-N-[2-(4-methoxyphenyl)-1-methylethyl]-N-methyl-benzamide;

2,3,4,5,6-pentafluoro-N-[2-(2-methoxyphenyl)-1-methylethyl]-N-methyl-benzamide;

2,3,4,5,6-pentafluoro-N-[2-(4-chlorophenyl)-1-methylethyl]-benzamide;

2-chloro-N-[2-(3-chloro-4-methoxyphenyl)ethyl]-benzamide;

N-[2-(2-bromophenyl)ethyl]-2-iodobenzamide;

2-bromo-N-[2-(3,4-dimethoxyphenyl)ethyl]-benzamide;

2,4-dichloro-N-[1-methyl-2-(3-tri-fluoromethyl phenyl)ethyl]-benzamide;

2-chloro-N-[2-(3,4-dimethoxyphenyl)ethyl]-benzamide;

2-chloro-N-[2-(4-chlorophenyl)-1-methyl-ethyl]-benzamide;

N-[2-3-chloro-4-methoxyphenyl)ethyl]-2-methyl]-benzamide;

N-[2-(3,4-dimethoxyphenyl)ethyl]-2-methylbenzamide;

2-(2-chloroethyl)-N-[2-(4-methoxyphenyl)ethyl]-benzamide; and $C_1$-$C_8$-alkylsulphonyl N-[2-(3-chloro-4-methoxyphenyl)ethyl]-2,6-diethylbenzamide.

2. The compound of claim 1 wherein each X is independently selected from the group consisting of a halogen atom, a (hydroxyimino)-$C_1$-$C_6$-alkyl group, a $C_1$-$C_8$-alkyl, a $C_1$-$C_8$-halogenoalkyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl and a ($C_1$-$C_6$-alkynyloxyimino)-$C_1$-$C_6$-alkyl.

3. The compound of claim 1 wherein $R^1$ and $R^2$ are independently selected from the group consisting of a hydrogen atom and a halogen atom.

4. The compound of claim 1 wherein $R^3$ and $R^4$ are independently selected from the group consisting of a hydrogen atom and $C_1$-$C_6$-alkyl.

5. The compound of claim 1 wherein $Y^a$ is selected from the group consisting of a halogen atom, a $C_3$-$C_6$-alkyl and a $C_1$-$C_6$-halogenoalkyl having 1 to 5 halogen atoms.

6. The compound of claim 1 wherein each Y is independently selected from the group consisting of a hydrogen atom and a halogen atom.

7. A process for the preparation of a compound of formula (I) of claim 1,

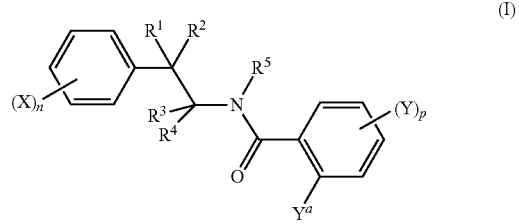

(I)

which comprises reacting a 1-alkyl-2phenylethylamine derivative of formula (II) or one of its salts

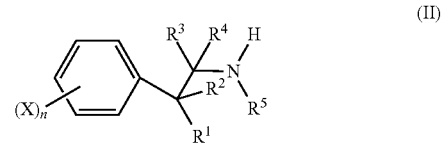

(II)

in which:

n is 1, 2, 3, 4 or 5;

each X is independently selected from the group consisting of a halogen atom, a nitro group, a cyano group, an amino group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a $C_1$-$C_8$-halogenoalkyl having 1 to 5 halogen atoms, a $C_7$-$C_8$-alkenyl, a $C_2$-$C_8$-alkynyl, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulanyl, a $C_1$-$C_8$ halogenoalkylsulfanyl having 1 to 5 halogen atoms, a $C_7$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_3$-$C_8$-cycloalkyl, a $C_3$-$C_8$-halogenocycloalkyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-allylcarbamoyl, a N-$C_1$-$C_8$-alkyloxycarbamoyl a $C_1$-$C_8$-alkoxycarbamoyl, a N-$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfenyl, a $C_1$-$C_8$-halogenoalkylsulfenyl having 1 to 5 halogen atoms, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkyl sulfonyl having 1 to 5 halogen atoms, a ($C_1$-$C_6$-alkoxyimino)-$C_1$-$C_8$-alkyl, a ($C_1$-$C_6$-alkenyloxyimino)-$C_1$-$C_6$-alkyl, a ($C_1$-$C_6$-alkynyloxyimino-$C_1$-$C_6$-alkyl, a (benzoyloxyimino)-$C_1$-$C_6$-alkyl, a benzyloxy, a benzylsulfanyl, a benzylamino, a phenoxy, a phenylsulfanyl and a phenylamino;

$R^1$ and $R^2$ are independently selected from the group consisting of a hydrogen atom, a $C_1$-$C_6$-alkyl and a $C_1$-$C_6$-alkyl-$C_3$-$C_7$-cycloalkyl;

$R^3$ and $R^4$ are independently selected from the group consisting of a hydrogen atom, a $C_1$-$C_6$-alkyl and a $C_1$-$C_6$-alkyl-$C_3$-$C_7$-cycloalkyl; and $R^5$ is selected from the group consisting of a hydrogen atom, a $C_1$-$C_6$-alkyl and a $C_3$-$C_7$-cycloalkyl;

with a carboxylic acid derivative of formula (III)

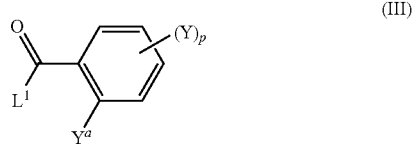

(III)

in which:
p is 1, 2, or 3;
each Y is independently selected from the group consisting of a hydrogen atom, a halogen atom, a $C_1$-$C_6$-alkyl and a $C_3$-$C_6$-halogenoalkyl;
$Y^a$ is selected from the group consisting of a halogen atom, a $C_1$-$C_6$-alkyl and a $C_1$-$C_6$-halogenoalkyl; and
$L^1$ is a leaving moiety selected from the group consisting of a halogen atom, a hydroxyl group, and —$OR^6$;
in which:
$R^6$ is selected from the group consisting of a $C_1$-$C_6$ alkyl a $C_1$-$C_6$ haloalkyl a benzyl, 4-methoxybenzyl, pentafluorophenyl and a group of formula:

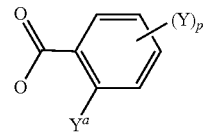

in the presence of a catalyst and, if $L^1$ is a hydroxyl group, in the presence of a condensing agent.

8. The process of claim 7 wherein $R^5$ is a hydrogen atom and the process further comprises completing by a further step according to the following reaction scheme:

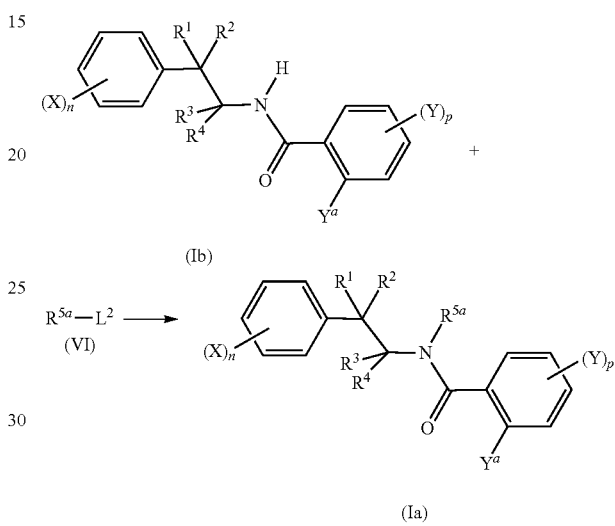

in which:
$L^2$ is a leaving moiety selected from the group consisting of a halogen atom, a 4-methyl phenylsulfonyloxy and a methylsulfonyloxy; and
$R^{5a}$ is selected from the group consisting of a $C_1$-$C_6$-alkyl group and a $C_3$-$C_7$-cycloalkyl;
wherein said further step comprises reacting a compound of formula (Ib) with a compound of formula (VI) to provide a compound of formula (Ia).

9. A fungicide composition comprising an effective amount of a compound according to claim 1 and an agriculturally acceptable support.

10. A method for combating the phytopathogenic fungi of plants comprising applying an effective and non-phytotoxic amount of the composition of claim 9 to the plant seeds or to the plant leaves and/or to the fruits of the plants or to the soil in which the plants are growing or in which it is desired to grow them.

11. The compound of claim 1 wherein:
each X is independently selected from the group consisting of a halogen atom, a (hydroxyimino)-$C_2$-$C_6$-alkyl group, a $C_1$-$C_8$-alkyl, a $C_1$-$C_8$-halogenoalkyl having 1 to 5 halogen atoms, a ($C_1$-$C_6$-alkoxyimino)-$C_1$-$C_6$-alkyl, a ($C_1$-$C_6$-alkenyloxyimino)-$C_1$-$C_6$-alkyl and a ($C_1$-$C_6$-alkynyloxyimino)-$C_1$-$C_6$-alkyl;
$R^1$ and $R^2$ are independently selected from the group consisting of a hydrogen atom and a halogen atom;
$R^3$ and $R^4$ are independently selected from the group consisting of a hydrogen atom and $C_1$-$C_6$-alkyl;
$Y^a$ is selected from the group consisting of a halogen atom, a $C_1$-$C_6$-alkyl and a $C_1$-$C_6$-halogenoalkyl having 1 to 5 halogen atoms; and each Y is independently selected from the group consisting of a hydrogen atom and a halogen atom.

12. A fungicide composition comprising an effective amount of a compound according to claim 11 and an agriculturally acceptable support.

13. A method for combating the phytopathogenic fungi of plants comprising applying an effective and non-phytotoxic amount of the composition of claim 12 to the plant seeds or to the plant leaves and/or to the fruits of the plants or to the soil in which the plants are growing or in which it is desired to grow them.

* * * * *